(12) United States Patent
Cole

(10) Patent No.: US 7,175,604 B2
(45) Date of Patent: Feb. 13, 2007

(54) AMBULATORY AID AND METHOD FOR PROVIDING AMBULATORY AID

(76) Inventor: Daniel Cole, 8717 Jackman Rd., Temperance, MI (US) 48182

( * ) Notice: Subject to any disclaimer, the term of this patent is extended or adjusted under 35 U.S.C. 154(b) by 136 days.

(21) Appl. No.: 11/057,610

(22) Filed: Feb. 14, 2005

(65) Prior Publication Data

US 2005/0182346 A1    Aug. 18, 2005

Related U.S. Application Data

(60) Provisional application No. 60/544,791, filed on Feb. 13, 2004.

(51) Int. Cl.
*A61F 5/00*    (2006.01)
*A63B 21/02*    (2006.01)

(52) U.S. Cl. .............. 602/28; 602/23; 482/124

(58) Field of Classification Search .................... 602/4, 602/20, 23, 28, 29, 62, 64, 65, 69; 128/876, 128/882; 482/121, 122, 124, 125, 139
See application file for complete search history.

(56) References Cited

U.S. PATENT DOCUMENTS

| | | | |
|---|---|---|---|
| 420,178 A | 1/1890 | Yagn | |
| 420,179 A | 1/1890 | Yagn | |
| 1,608,032 A | 11/1926 | McNabb | |
| 1,618,273 A * | 2/1927 | Davidson | ............. 482/124 |
| 2,097,376 A | 10/1937 | Marshman | |
| 3,295,517 A | 1/1967 | Stevens | |
| 4,329,982 A | 5/1982 | Heaney | |
| 4,566,447 A | 1/1986 | Deis | |
| 5,112,296 A | 5/1992 | Beard et al. | |
| 5,186,701 A | 2/1993 | Wilkinson | |
| 5,308,305 A | 5/1994 | Romney | |
| 5,362,295 A | 11/1994 | Nurge | |
| 5,372,565 A | 12/1994 | Burdenko | |
| 5,865,203 A | 2/1999 | Villano | |
| 6,361,517 B1 | 3/2002 | Slinger | |
| 2003/0195091 A1* | 10/2003 | Webber et al. | ............. 482/100 |

* cited by examiner

*Primary Examiner*—Henry Bennett
*Assistant Examiner*—Shumaya B. Ali
(74) *Attorney, Agent, or Firm*—John C. Purdue; David C. Purdue

(57) ABSTRACT

A device including an elastic member and means for connecting the ends of it to a person so that the elastic strip is operable, when the person's leg is straight or nearly straight, to exert a force that tends to bend the leg at the knee and hip is disclosed. The device assists someone using the device to achieve a safe and adequate lift of his or her legs during the swing phase of the gait cycle. Prolonged use of the device has been observed to cause a person, when later walking without the device, to exhibit better leg lift during the swing phase of the gait cycle than that person did before using the device. The elastic strip can be connected at one end to a shoe insert and, at the other end, to a belt.

9 Claims, 4 Drawing Sheets

AMBULATORY AID AND METHOD FOR PROVIDING AMBULATORY AID

BACKGROUND OF THE INVENTION (1) Field of the Invention

The present invention relates generally to devices that provide aid to persons while they are walking and is especially geared towards assisting persons who have difficulty achieving foot clearance during the swing phase of their gait cycle.

(2) Description of Related Art Including Information Disclosed Under 37 CFR 1.97 and 37 CFR 1.98

A remarkable number of devices have been proposed as aids to walking and or exercise. Some examples can be found in U.S. Pat. Nos. 420,178; 420,179; 1,608,032; 2,097, 376; 3,295,517; 4,329,982; 4,566,447; 5,112,296; 5,186, 701; 5,308,305; 5,362,295; 5,372,565; 5,865,203; and 6,361,517. It appears, however, that none of the devices disclosed in these patents is intended to provide or capable of providing assistance to a person in lifting his leg during the swing phase of that person's gait cycle.

A substantial number of persons fail to lift their legs enough during the swing phase of the gait cycle. This is a dangerous deficiency because it makes those people prone to tripping or stumbling over even the smallest obstacles. The problem is most risky for elderly persons who are at a higher risk than the general population for broken bones and, in particular, broken hips and the like.

U.S. Pat. No. 6,361,517 ("Slinger") discloses a foot lift assist device for enabling a person with drop foot to walk in a nearly normal manner. The Slinger device includes a foot strap that is worn on the toot generally over the toes of the foot. One end of an elastic cord is connected to a ring on the foot strap that is located outside of the centerline of the foot while the other end of the elastic cord is connected or anchored at the person's hip, for example, to a belt. According to the Slinger patent, when a person removes his weight from the foot that has the device attached, the elastic cord exerts an upward force that bends the leg at the knee and hip and exerts an upward force that also pivots the foot upwardly about the ankle. It is noted, however, that when a user's leg is straight, the force exerted by the elastic cord, rather than exerting a force that bends the leg at the knee, it exerts a force that tends to lock the knee and hold the leg straight. It is only after a user of the Slinger device has bent his knee substantially, against the force exerted by the elastic cord, that the elastic cord becomes operable to exert a force that tends to bend the leg at the knee and the hip.

BRIEF SUMMARY OF THE INVENTION

The present invention is device including an elastic member and means for connecting it to a person so that the elastic strip is always operable to exert a force that tends to bend or flex the leg at the knee and hip, thereby assisting persons using the device to achieve a safe and adequate lift of their legs during the swing phase of their gait cycles. Initial research concerning the device of the present invention indicates that the device has an additional benefit beyond providing direct leg lift assistance during the swing phase of the gait cycle. It has been observed that a person who has used the device of the present invention for a period of time will, when walking without the device, exhibit better leg lift during the swing phase of the gait cycle than that person did before using tile device.

Accordingly, it is an object of the present invention to provide a device imparts a bias to a leg tending to lift the leg and bend the leg at the knee and the hip at all times.

It is a further object of the invention to provide a simple device that will assist people who do not achieve adequate leg lift during the swing phase of their gait cycle to achieve adequate leg lift to reduce the risk of stumbling or tripping.

It is a still further object of the present invention to provide a simple device which can effect a positive change in swing phase leg, lift performance after it has been used for a while.

These and other objects and advantages of the present invention will be fully appreciated by those skilled in the art upon reviewing the disclosures herein.

DETAILED DESCRIPTION OF THE PREFERRED EMBODIMENTS

Figure 1:
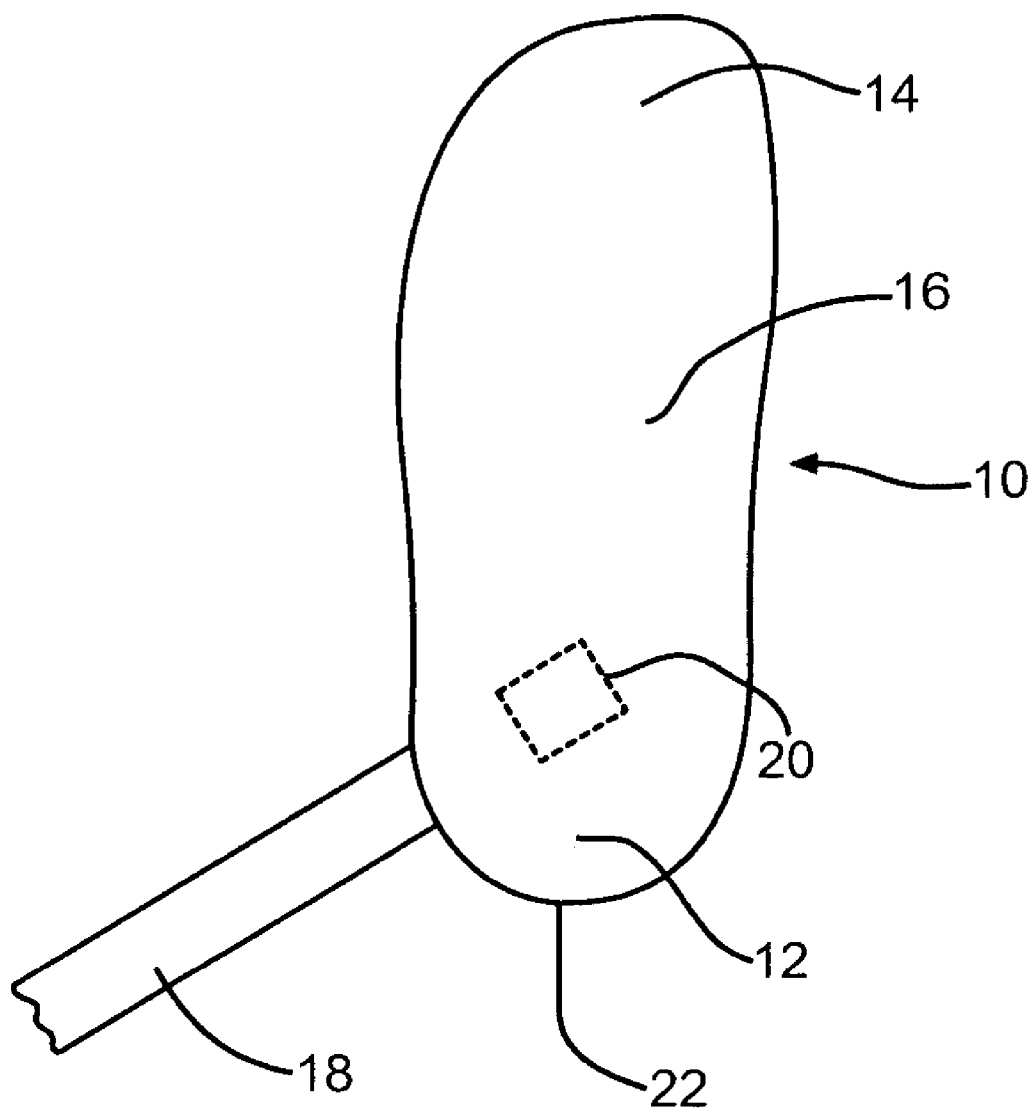
FIG. 1 is a top view of a shoe arch support and an attached elastic leg strap which make up part of the device according to the present invention.

Referring to FIG. 1, a left shoe insert 10 is illustrated. The insert 10 comprises a heel portion 12 and a toe portion 14. It is preferred that an arch support 16 is also provided on the insert 10. An elastic member comprising an elastic leg strap 18 is connected to the insert 10 by stitching as indicated at 20. The left shoe insert provides a means for connecting the elastic leg strap 18 to a left shoe. It is preferred that, as shown in FIG. 1, the elastic leg strap 18 is connected to the bottom of the insert 10 so that, when the insert 10 is placed within a shoe., the elastic leg strap will be between the insert 10 and the bottom of the shoe. It will be appreciated that the elastic leg strap 18 can be connected to the insert 10 by any suitable means including, but not limited to, glue or adhesive and mechanical fasteners including, but not limited to snaps, hook and loop fasteners, rivets, staples, threaded fasteners and the like.

As shown in FIG. 1, the elastic leg strap 18 is connected to the heel portion 12 of the shoe insert 10. It is preferred, as shown in FIG. 1, that the elastic leg strap 18 be connected to the insert so that it extends from the point where it is connected to the left shoe insert 10, to the left and towards a real or heel edge 22 of the insert 10. A device according to the invention may also include a right shoe insert (not shown) that would be a mirror image of the left shoe insert 10. A device according to the present invention may include only a right shoe insert and elastic leg strap. In a right shoe insert, the elastic leg strap would extend from the point where it is connected to the insert to the right and towards the real or heel edge of the right shoe insert. It will be appreciated that the exact location of the connection point between the elastic leg strap and a left or right shoe insert is not critical. Essentially, however, the elastic leg strap 18 must be connected to the shoe insert 10 in such a manner that, when the insert 10 is positioned within a shoe and a foot is inserted into the shoe on top of the insert 10 and tension is applied to the elastic leg strap so that the elastic leg strap tends to lift the shoe, the insert 10 and the foot therein, the lifting force acts on the insert 10 on the rear half of the insert and, preferably, on the outside of the insert 10. i.e., the left side for a left shoe insert and the right side for a right side shoe insert.

Figure 2:
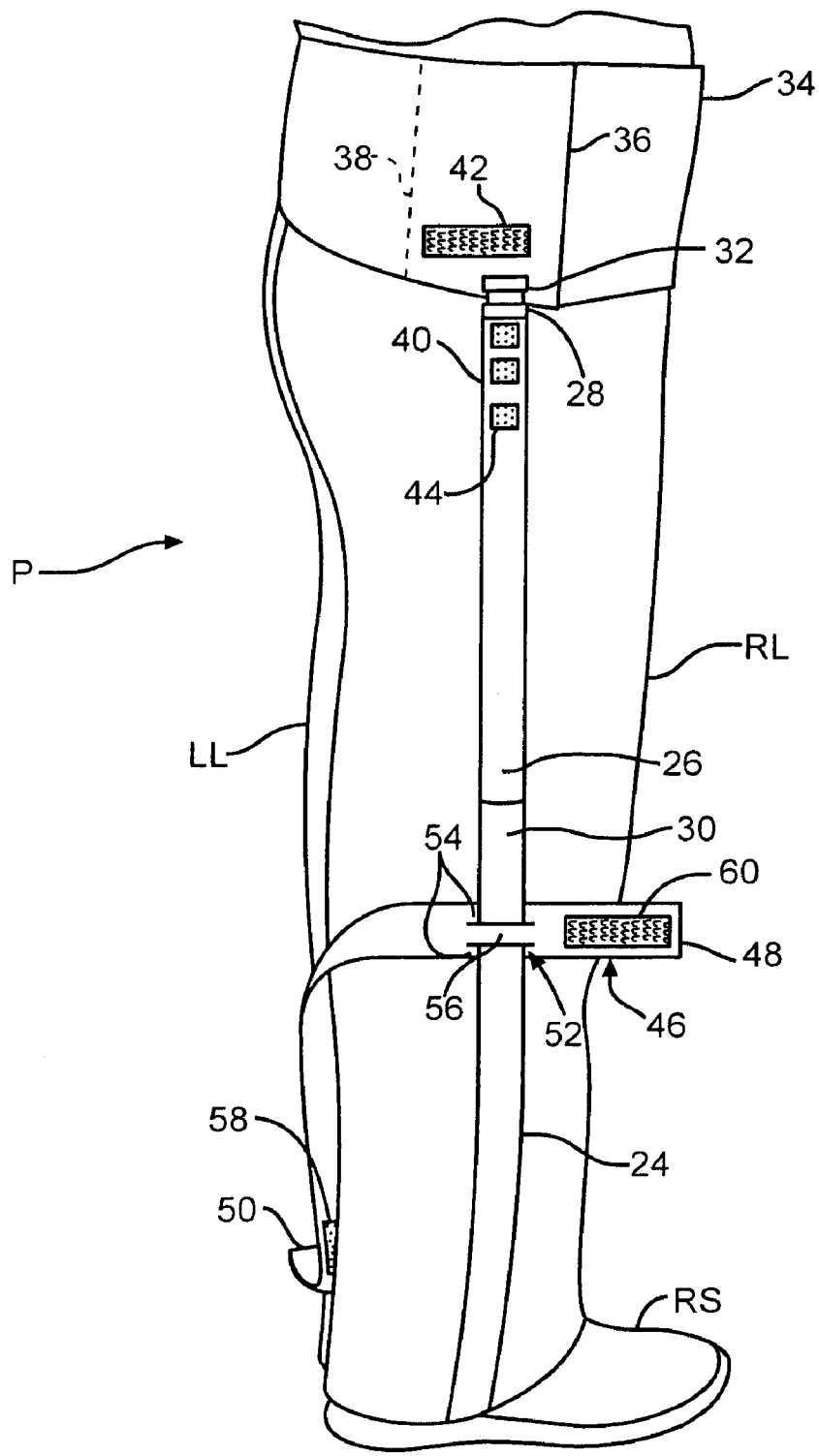
FIG. 2 is a side view of a part of a person showing, the device of the present invention partially secured to the person.

Turing now to FIG. 2, a right elastic leg strap 24 is positioned alongside a right leg RL of a person indicated generally at P. A lower end (not shown) of the right elastic leg strap 24 is positioned within a right shoe RS and is connected, inside of the shoe RS, to a right shoe insert (not shown) as described above. A second or upper end 26 of the right elastic leg strap 24 has been fed through a cinching buckle 28 and is hanging down adjacent to a middle portion 30 of the right elastic leg strap 24. The cinching buckle 28 is supported on a tab 32 that is securely connected to a waist belt 34 that is secured about the waist of the person P. The waist belt 34 comprises a first end 36 that overlaps a second end 38 and the overlapping portions are connected together by any suitable means such as hook and loop fasteners or other mechanical fasteners (not shown), Alternatively, the belt 34 might be provided with straps and buckles (not shown). It is preferred that the belt 34 be elastic so that it can be fitted snugly and securely to the person P and so that tensile forces exerted against the belt 34 are distributed broadly through the belt 34. In place of the belt 34 a conventional belt of the type typically used to hold Lip trousers may be used. An elastic belt having a substantial width, such as the belt 34, is strongly preferred, however.

As an alternative to the cinching buckle 28, hook and loop fasteners are illustrated for attaching an upper portion 40 of the right elastic leg strap 24 to the belt 34. A hook strip 42 is secured by stitching, adhesive or other suitable means to the outside of the waist belt 34. A plurality of loop strips 44 are secured to the upper portion 40 of the right elastic leg strap 24. Regardless of whether the elastic leg strap 24 is secured to the belt 34 by a cinching buckle 28, hook and loop fasteners 42 and 44 or some other means, when the elastic leg strap 24 is so connected, it must be stretched or tensioned, as described in more detail below.

A thigh strap 46 having a first end 48 and a second end 50 is slit at 52 so that the elastic leg strap 24 can be held between two rear portions 54 and a front portion 56 of the thigh strap 48. This arrangement allows the elastic leg strap 24 to slide up and down relative to the thigh strap 46 but constrains the elastic leg strap 24 from moving around a person's thigh. In other words, the thigh strap 46 cooperates with the elastic leg strap 24 to maintain the leg strap 24 in a fixed circumferential location relative to the thigh of a person P. It is preferred that the thigh strap be elasticized. Connectors are provided on the ends 48 and 50 of the thigh strap 46 and hook and loop fasteners comprising a hook strip 58 and a loop strip 60 are the preferred type of connectors. The hook strip 58 and the loop strip 60 are secured by stitching, adhesive or other securing means to the first and second ends 48 and 50 of the thigh strap 46.

Figure 3:
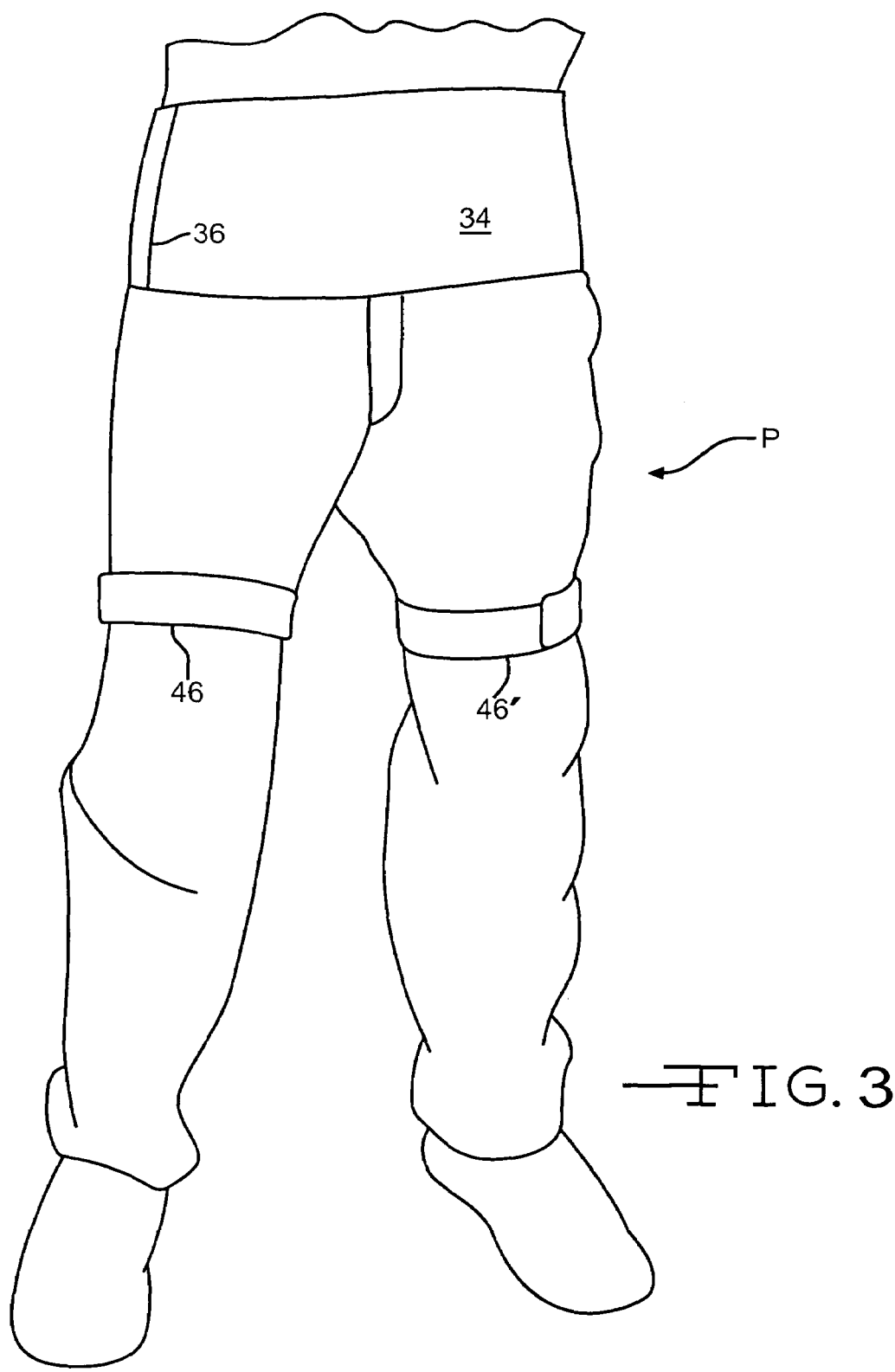
FIG. 3 is a front view of the person shown in FIG. 2 showing the device fully secured to that person in an operative way.

Turning now to FIG. 3, a person P has on the device of the present invention. The right elastic leg strap 24 (not show) is secured between the right shoe insert I 0 (not shown) and the waist belt 34. A left elastic leg strap (not shown) corresponding with the right elastic leg strap is secured between a left shoe insert (not shown) corresponding with but a mirror image of the right shoe insert 10 (not shown) and the waist belt 34. The elastic leg straps are connected to the waist belt 34 so that when the person's legs are straight, as shown in FIG. 3, the elastic is tensioned. Further, the elastic leg straps are positioned at the rear of the person's feet on the outside, behind the person's knees on the outside and behind the persons limps on the outside so that, due to the tension in the elastic leg straps, the straps are operable to exert a force on the person's legs tending to bend or flex the legs at the knee and the hip, and to lift the person's feet. When the person is walking, and is in the swing phase of the person's gait, the leg that is swinging will be acted on by the elastic strap associated with that leg. Specifically, the strap will exert a lifting force on the associated foot and exert a force operable to tend to cause the leg to bend or flex at the knee and the hip.

Figure 4:
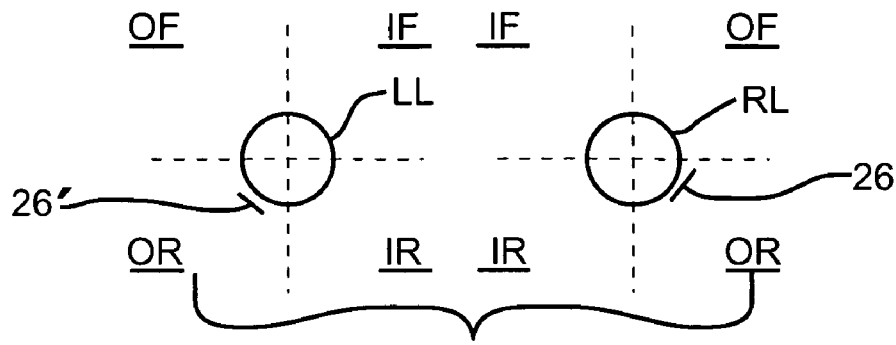
FIG. 4 is a cross sectional view through lower portions, next to the feet, of a left leg LL and a right leg RL of the person, P in FIG. 3

Referring now to FIG. 4, cross sections through the lower portions, next to the feet, of a left leg LL and a right leg RL of the person P in FIG. 3 are illustrated. Four quadrants are illustrated for each lower leg portion. The left leg LL has an outer front quadrant OF, an inner front quadrant IF, an inner rear quadrant IR and an outer rear quadrant OR. The right leg RL has an outer front quadrant OF, an inner front quadrant IF, an inner rear quadrant IR and an outer rear quadrant OR. The elastic leg strap 26 associated with the right leg RL is positioned in the outer rear OR quadrant of the right leg. A corresponding elastic leg strap 26' that is associated with the left leg LL is also positioned in the outer rear OR quadrant of the left leg. This positioning of the elastic straps 26 and 26' in the vicinity of the lower portions of the right and left legs is achieved and maintained by the right and left shoe inserts (not shown) as described above with reference to FIG. 1.

Figure 5:
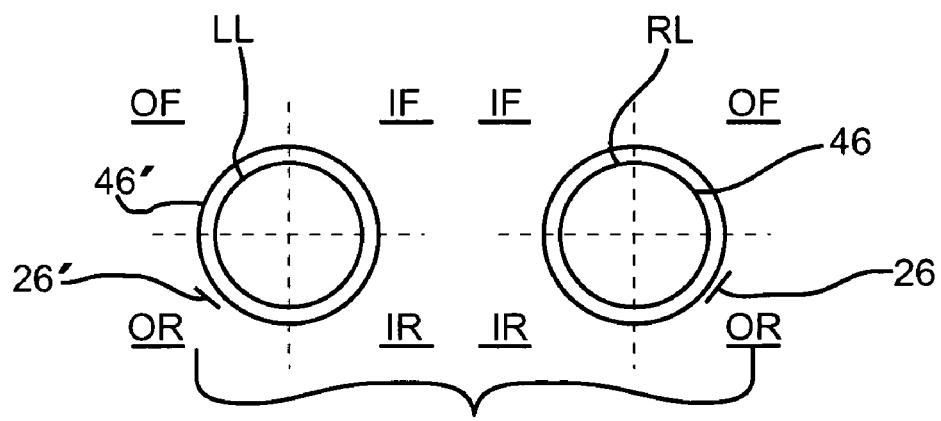
FIG. 5 is a cross sectional view through the thigh portions of the left leg LL and the right leg RL of the person P in FIG. 3.

Referring now to FIG. 5, cross sections through the thigh portions of a left leg LL and a right leg, RL of the person P in FIG. 3 are illustrated. Four quadrants are illustrated for each thigh leg portion. The left leg LL has an outer front quadrant OF, an inner front quadrant IF, an inner real quadrant IR and an outer rear quadrant OR. The right leg RL has an outer front quadrant OF, an inner front quadrant IF, an inner real quadrant IR and an outer real quadrant OR. The elastic leg strap 26 associated with the right leg RL is positioned in the outer real OR quadrant of the right leg in the thigh region. A corresponding elastic leg strap 26' that is associated with the left leg LL is also positioned in the outer real OR quadrant of the left leg in the thigh region. This positioning of the elastic straps 26 and 26' in the vicinity of the thigh portions of the right and left legs is achieved and maintained by the right thigh strap 46 and a left thigh strap 46' (FIGS. 3 and 5) and by positioning tile slits 52 thereof in the outer rear quadrants OR of the right and left leg, respectively.

Figure 6:
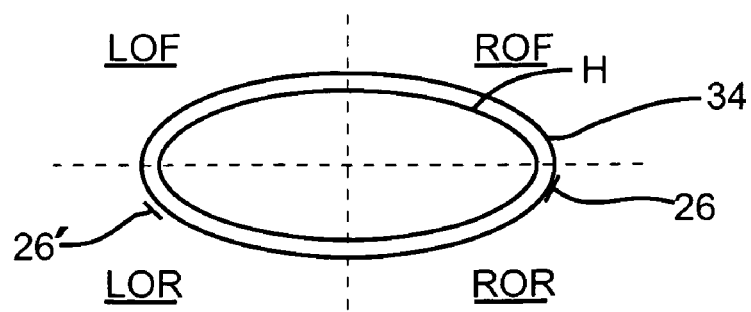
FIG. 6 is a cross sectional view through the hips H of the person P in FIG. 3.

Referring now to FIG. 6, a cross section through the hips H of the person P in FIG. 3 is illustrated. Four quadrants are illustrated for the hip portion. The hips have a left outer front quadrant LOF, a right outer front quadrant ROF, a right outer rear quadrant ROR and a left outer real quadrant LOR. Tile elastic leg strap 26 associated with the right leg is positioned in the right outer rear ROR quadrant of the hips H. The corresponding elastic leg strap 26' that is associated with the left leg LL is positioned in the left outer real LOR quadrant of the lips H. This positioning of the elastic straps 26 and 26' in the vicinity of the hips is achieved and maintained by the position of the cinching buckles on the waist belt 34.

The tension in the elastic legs straps is preferably adjustable through the cinching buckle or the hook and loop fasteners or other means for connecting the elastic leg straps to the waist belt. Tile most effective tension or the elastic leg straps may vary from person to person and can be readily determined by trial and error.

The invention claimed is:

1. An ambulatory aid comprising, in combination:
   a) an insert for a shoe to be worn by a person, said insert having upper and lower surfaces, a toe end and a heel end, and
   b) a foot lift assist comprising:
      i) a belt to be worn over the hips of a person, and
      ii) an elastic member having a first end connected to a selected lateral section of said belt, and a second end connected to the bottom of said insole at a point which is closer to the heel end thereof than to the toe end, so that a person wearing the insert and the foot lift assist is helped to walk by an upward force exerted by the insert on the wearer's foot.

2. The ambulatory aid claimed in claim 1 wherein said insert is for a left shoe, and said elastic member is connected to the left outer rear quadrant of said belt.

3. The ambulatory aid claimed in claim 1 wherein said insert is for a right shoe, and said elastic member is connected to the right outer rear quadrant of said belt.

4. An ambulatory aid comprising, in combination:
   a) an insole in a shoe worn by a person, said insole having upper and lower surfaces, a toe end and a heel end, and
   b) a foot lift assist comprising:
      i) a belt worn over the hips of the person, and
      ii) an elastic member having a first end connected to a selected lateral section of said belt, and a second end connected to the bottom of said insole at a point which is closer to the heel end thereof than to the toe end, so that the person wearing the insole and the foot lift assist is helped to walk by an upward force exerted by the insole on the person's foot.

5. The ambulatory aid claimed in claim 4 wherein said insole is for a left shoe, and said elastic member is connected to the left outer rear quadrant of said belt.

6. The ambulatory aid claimed in claim 4 wherein said insole is for a right shoe, and said elastic member is connected to the right outer rear quadrant of said belt.

7. An ambulatory aid comprising, in combination:
   a) an insert for a shoe to be worn by a person, said insert having upper and lower surfaces, a toe end and a heel end, and
   b) a foot lift assist comprising:
      i) a belt to be worn over the hips of a person, and
      ii) an elastic member having a first end connected to a selected lateral section of said belt, and a second end connected to the bottom of said insole at a point which is closer to the heel end thereof than to the toe end, so that a person wearing the insert and the foot lift assist is helped to walk by an upward force exerted by the insert on the wearer's foot and so that when that person is walking and that person is in the swing phase of his or her gait, the device exerts a force operable to cause the person's leg that is associated with the shoe insert to bend or flex at the knee and the hip.

8. The ambulatory aid claimed in claim 7 wherein said insert is for a left shoe, and said elastic member is connected to the left outer rear quadrant of said belt.

9. The ambulatory aid claimed in claim 7 wherein said insert is for a right shoe, and said elastic member is connected to the right outer rear quadrant of said belt.

* * * * *